(12) United States Patent
Most et al.

(10) Patent No.: US 6,284,892 B1
(45) Date of Patent: Sep. 4, 2001

(54) METHOD FOR PRODUCING SALTS OF CYCLIC AMIDINES

(75) Inventors: Dieter Most, Bruchkoebel; Karlheinz Drauz, Freigericht, both of (DE)

(73) Assignee: Degussa Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/555,519

(22) PCT Filed: Dec. 7, 1998

(86) PCT No.: PCT/EP98/07373

§ 371 Date: Jun. 7, 2000

§ 102(e) Date: Jun. 7, 2000

(87) PCT Pub. No.: WO99/29665

PCT Pub. Date: Jun. 17, 1999

(30) Foreign Application Priority Data

Dec. 8, 1997 (DE) ................................. 197 54 322

(51) Int. Cl.[7] ...................... C07D 211/56; C07D 211/60; C07D 207/00
(52) U.S. Cl. ....................... 546/244; 546/245; 548/531
(58) Field of Search ................... 546/247, 245; 548/531

(56) References Cited

FOREIGN PATENT DOCUMENTS

WO/9422828 * 10/1994 (WO) ................................. 546/244

OTHER PUBLICATIONS

J. Barleunga, et al. Synthesis, "Tandem Amidomercuration–alkylation of alkenes. One pot synthesis of amidic 1,4–bifuctionalized compoounds.", pp 831–832, 1984.*

* cited by examiner

Primary Examiner—Joseph K. McKane
Assistant Examiner—Joseph Murray
(74) Attorney, Agent, or Firm—Oblon, Spivak, McClelland, Maier & Neustadt, P.C.

(57) ABSTRACT

The present invention relates to a process for the production of salts of cyclic amidines of the general formula (I)

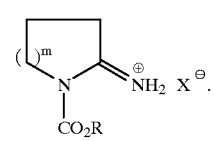

Figure 1:
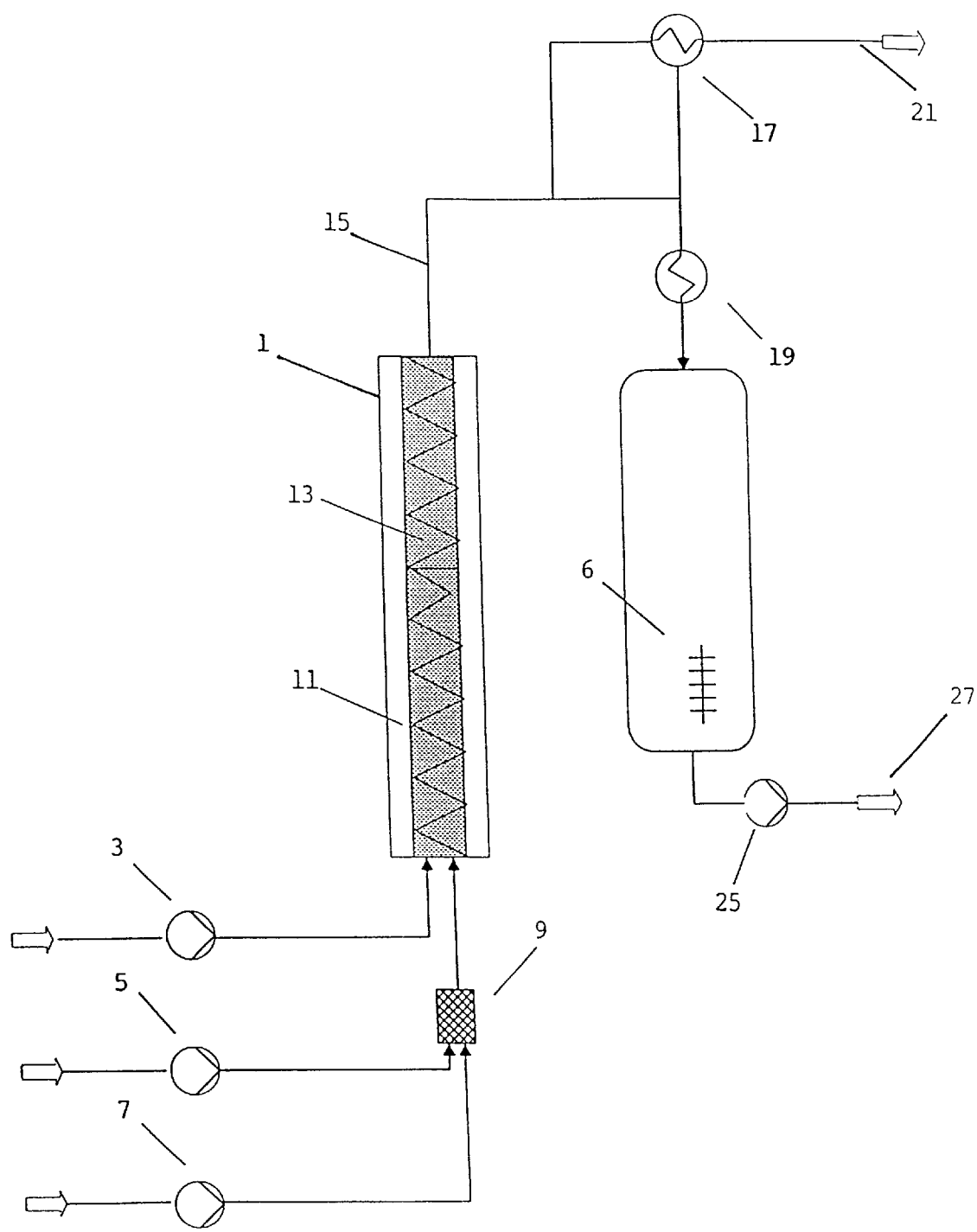

The processes described hitherto as prior art enable salts of the compound (I) to be produced only at low yields. As a result of protecting ω-amino-α-amino acids selectively at the ω-amino function, oxidative decarboxylation of the latter protected compounds by means of halogen derivatives, and subsequent cyclisation of the oxidatively decarboxylated substances with the addition of acid, according to the invention salts of the compound (I) are achieved in better yields.

36 Claims, 2 Drawing Sheets

METHOD FOR PRODUCING SALTS OF CYCLIC AMIDINES

The present invention relates to a process for the production of compounds of the general formula (I)

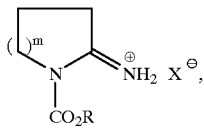

wherein $X^\ominus$ represents an inorganic anion, m=1, 2 or 3, and R represents a linear $(C_1-C_4)$-alkyl radical.

Compounds of the above structural type are advantageous intermediates for the production of bioactive ingredients such as are known from U.S. Pat. No. 4,213,773 and WO 94/22828.

WO 94/22828 describes the possibility of cyclising N-(4-cyanobutyl) carbamic acid alkyl esters by means of an anhydrous hydrogen halide. The yields of the latter reaction are not mentioned. A paper published in Synthesis 1984, 831 is referred to for the production of the N-(4-cyanobutyl) carbamic acid alkyl ester. However, the process indicated therein affords only a maximum 32% yield of the latter compound. That is to say that according to the prior art the maximum possible total yield of the production of (I), when m=2 and R=Me, is 32%. Furthermore, a mercury salt is used in the latter process, for ecological reasons a practical impossibility on a large industrial scale. In order to produce N-(4-cyanobutyl) carbamic acid methyl ester it is necessary according to the Synthesis process to pass the ethene which is to be used through a liquid solution of methyl carbamate and mercury nitrate in dichloromethane, which is under reflux. Apart from the tendency of ethene to polymerise when in contact with Lewis acids or Lewis bases and radicals, the storage of this high-risk chemical, necessary for a large-scale industrial operation, is extremely questionable. the object of the invention was consequently to find a process for the production of compounds of the general formula (I), which improves on the prior art as regards both economic and ecological considerations and affords a lower-risk, stable process sequence on a large industrial scale.

The latter and other objects not further specified are achieved by a process in accordance with the features of the characterising part of claim 1. Particularly advantageous embodiments of the process are provided by the sub-claims dependent on claim 1.

Very good total yields of >70% of the desired compounds are achieved in a robust process without the occurrence of ecologically questionable wastes, as a result of the reaction of a corresponding enantiomer-pure or racemic ω-amino-α-amino acid in selective manner at the ω-amino function thereof to give compounds of the general formula (II)

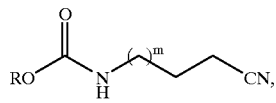

oxidative decarboxylation of the compounds (II) thus obtained to give substances of the general formula (III)

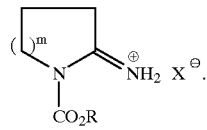

and reaction of the compound (III) with the exclusion of water in the presence of an acid, with ring closure, to give the salt of the general formula (I)

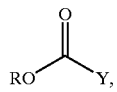

It is a further advantage of the latter process that all the solvent streams can be largely circulated, thus reducing the volume of unavoidable waste to the maximum possible degree.

It is particularly advantageous to react the corresponding ω-amino-α-amino acid or a precursor of the latter carboxylic acid, under basic conditions with a reagent of the general formula (IV)

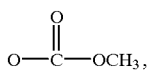

wherein Y=Cl, Br or OMe or $$O-\overset{\overset{O}{\|}}{C}-OCH_3,$$

and R=$(C_1-C_4)$-alkyl present preferably in linear form, or aryl, to give compounds of the general formula (II). Precursors of ω-amino-α-amino acids, which are considered here are commercially obtainable hydrochlorides and hydrates thereof or compounds in the form of their free bases as approximately 50% aqueous solutions. In a particularly preferred case the ω-amino-α-aminocarboxylic acid is lysine. Such reactions are in principle known from Houben-Weyl 1977, Vol. XV/I, pp. 468 et seq., but the use of dimethyl carbonate (DMC) is particularly advantageously suitable for affording exceptionally highly selective protection to the ω-amino-α-amino acid only at its ω-amino function.

The choice may be made to introduce the latter protective group in a two-phase system prepared from water and a water-immiscible organic solvent. In this case organic solvents which have proved valuable are aliphatic hydrocarbons, chlorinated hydrocarbons and aromatic hydrocarbons, or ethers and ketones. Suitable aliphatic hydrocarbons are n-pentane, n-hexane, n-heptane, cyclopentane, cyclohexane, methylcyclohexane, petroleum ether, ligroin.

Particularly suitable chlorinated/brominated hydrocarbons are chloroform, methylene chloride, 1,1,1-trichloroethane, 1,1,2-trichloroethane, 1,2-dichloroethane, bromoform, dibromomethane, 1,2-dibromoether.

Suitable aromatic hydrocarbons are toluene, 1,2-, 1,3-, 1,4-xylene, mesitylene.

Ethers which are considered are diethyl ether, methyl tert.-butyl ether, 1,2-diethoxyethylene.

Particularly preferred ketones are methyl isobutyl ketone, diethyl ketone, diisopropyl ketone, tert.-butyl methyl ketone.

An advantageous embodiment of the aforementioned process is likewise formed by the reaction of ω-amino-α-amino acids, or a precursor of the latter carboxylic acids in a single-phase system prepared from water with the reagent of the general formula (IV), the use of DMC is particularly advantageous. A water-miscible organic solvent may optionally be added to the latter system. The following have proved to be suitable water-miscible organic solvents: alcohols such as, for example, methanol, ethanol, isopropanol, propanol, tert.-butanol, sec-butanol, isobutanol, glycol. Further water-miscible organic solvents are ethers such as, for example, THF, 1,2-dimethoxyethane or diethylene glycol, dioxane.

When DMC is used as the acylation reagent in the aforementioned reaction it is advantageous to work with DMC in excess such as to afford the ω-amino-α-amino acid used the maximum possible ω-protection. The excess may be up to 10 times the equivalent quantity of DMC compared with the ω-amino-α-amino acid. An excess of 3–5 eq. is particularly preferred.

It is advantageous to introduce the (ω-amino-α-amino acids or the precursors of the latter carboxylic acids as an aqueous basic solution and dispense the DMC diluted with an organic solvent into the solution, or to admix the DMC as such. If organic diluents are used, the single-phase or two-phase systems described above then arise, depending on whether the latter are water-miscible or water-immiscible. The use of DMC pure always results in a single-phase system.

Advantageously, the unused excess of DMC collects in the organic, upper phase, when a two-phase reaction medium is used, and can be recycled in simple manner by phase separation without the risk of excessive saponification in the aqueous basic, lower phase.

In order to reduce DMC saponification as far as possible and achieve short reaction times and high yields, it is always advantageous to work with very thorough intermixing of the two phases. This correspondingly thorough mixing can be achieved by particular stirrer units or pumps such as, for example, regenerative pumps, jet mixers, nozzle systems, venturi mixers or ejector pumps, and the like. When the single-phase working method is used, the DMC is introduced into the basic aqueous solution of ωamino-α-amino acid or the precursor of the latter carboxylic acid, with equally thorough intermixing. It is advantageous here to isolate the excess DMC after the reaction by extracting it with a water-immiscible organic solvent, and to recycle it. The DMC thus recovered can be used again in a subsequent working cycle.

In order to reduce to the greatest possible extent the—hydrolysis—reaction which competes with the introduction of the protective group, the ω-amino-α-amino acid is reacted with the DMC within the pH range >8 to <14, preferably 10–13, and most particularly preferably 11–12. The following may be used as bases which are useful for adjusting the pH: alkali metal/alkaline earth metal bases or amine derivatives. NaOH, KOH, Ca(OH)$_2$, Ba(OH)$_2$, Na$_2$CO$_3$, NaHCO$_3$, K$_2$CO$_3$, KHCO$_3$ or NH$_4$OH, (NH$_4$)$_2$CO$_3$, NH$_4$HCO$_3$ preferably serve to regulate pH in this reaction.

The reaction temperatures should likewise be between 5° C. and 25° C., preferably 10–20° C., and most particularly preferably around 15° C.

The aqueous ω-Moc-amino-α-amino acid solution thus obtained then contains in addition to the product of the general formula (II) only a little educt, plus Bis-Moc-(II) and α-Moc-(II) as by-products, and a certain salt load. It may, notwithstanding, be used in advantageous manner for the subsequent oxidative breakdown without further purification steps.

Other acylation reagents derivable from the general formula (IV) may serve in equivalent manner to produce ε-alkoxycarbonyl lysine.

In the aforementioned aqueous solution, according to the invention the compounds of the general formula (II)

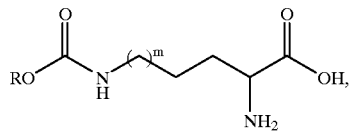

undergo oxidative decarboxylation with an oxidant taken from the group comprising halogens or halogen derivatives, to give compounds of the general formula (III)

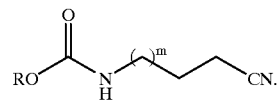

The latter reaction is known in principle from the literature (Synth. Meth. 1982, 13, 548), but has not hitherto been described for reacting species of the general formula (II). The compounds chlorine and bromine are advantageously used as halogens for the oxidation. Examples of suitable halogen derivatives are, inter alia: hypochlorite, chlorite, trichloroisocyanurate, dichloroisocyanurate, chloramine-T, N-chlorosuccinimide, 1,3-dichloro-5,5-dimethylhydantoin, 1-chloro-3-bromo-5,5-dimethylhydantoin, N-chlorosuccinimide, hypobromite, bromate/bromide, bromochloride, 1,3-dibromo-5,5-dimethylhydantoin, 1-chloro-3-bromo-dimethylhydantoin, N-bromosuccinimide, methylhypobromite. Elemental bromine and oxidants derivable from bromine, in particular BrCl and mixtures of NaOCl and NaBr, are particularly preferred. Their selectivity is markedly superior to that of chlorine and oxidants derived from chlorine, and they have a greatly reduced tendency to over-oxidise.

The derivatives (II) are advantageously oxidised in aqueous solution to which organic solvents may optionally be added. The aforementioned water-miscible solvents are considered as the organic solvents.

An advantageous embodiment of the process described above in this case results without intermediate isolation of the compound (II), as described above. When the protective group is introduced in a two-phase system, the organic phase is separated from the aqueous phase after the reaction. The aqueous phase in which (II) is present quantitatively can be used for the oxidation without further treatment. When the protective group is introduced in homogeneous phase the necessary phase separation is omitted. In this case, after extraction of the DMC the compound of the general formula (II) may be reacted immediately with the oxidants indicated above. The by-products present in the aqueous phases do not interfere with the oxidation of (II) to the compound (III). On the other hand, it is also possible, and is advantageous for obtaining a product (III) of maximum purity, for (II) to be isolated as a solid from its aqueous product phase by acidification and, in a separate step, to be then oxidised with halogens or halogen derivatives in an aqueous solution.

Oxidation is carried out according to the invention at between −10° C. and 60° C. The range here is preferably 20–50° C., most particularly preferably 30–40° C. To achieve the most complete oxidation possible at least 2 eq. of oxidant are necessary (for example 2 mole Br$_2$ per mole (II)). It is preferable to work with an excess of 2–4 eq., particularly preferably with 2–3 eq. and most particularly preferably 2–2.5 eq.

Two variants are in principle advantageous for the oxidation. One starts with an aqueous solution of (II) which is adjusted to pH 11 to 12. The oxidant, diluted or undiluted, is dispensed into the latter solution. The solvents discussed above, such as alcohols or chlorinated/brominated hydrocarbons, ethers and water, are suitable diluents.

Another particularly advantageous method starts with the diluted or undiluted oxidant, and a solution of (II) adjusted to pH 11 to 12 is dispensed into the latter. The solvents mentioned above are again suitable as diluents for the oxidant. This method ensures that an excess of oxidant is present at all times. This suppresses side-reactions such as, for example, hydrolysis of the intermediate products of oxidation, and affords the maximum product yield. Advantageously, the pH during oxidation is within the range 6 to 13, preferably 7 to 11, most particularly preferably 8 to 10.

The reaction step just described may optionally be carried out batch-wise. It consequently represents that section of the process for synthesising the compound (I), which is critical to success. Most particularly advantageously, very good yields are obtained in this oxidation when the oxidant and the species which is to be oxidised are present in a specific ratio to one another. This advantageous ratio reduces the occurrence of undesirable side-reactions. If, for example, the end product of the oxidative breakdown (III) comes into contact with excessive oxidant, the result is an increase in products of over-oxidation. If, on the other hand, too little oxidant is present during oxidation, the further reaction of intermediate products of oxidation is slowed down, such that the latter are hydrolysed to a greater degree in the basic reaction medium.

An advantageous solution to the problem outlined above is to carry out the reaction in apparatus or means of reaction in which a local concentration profile can be adjusted, with, however, an approximately constant concentration of the reagents prevailing in a given location, the latter consequently therefore being constant as to time.

In this case, the species which is to be oxidised (II), which is in the aqueous phase is pumped through the latter apparatus, and the oxidant is dispensed in at one or more points, or vice versa. This ensures according to the invention the presence of a local concentration profile as to substrate and reagent, which can be regulated in a manner which is individual and advantageous to the reaction by way of the starting concentration of (II) and the quantity of oxidant which is dispensed-in. The result is minimal by-product formation and yields of the desired nitrile (III) which, in the optimum case, are around approximately 90% or more. The procedure described above is advantageous particularly on a large industrial scale, because disruptions inherent in the system as a result of the additional regulation potential, such as are an unavoidable part of a large-scale industrial batch process, can in this case be detected and reduced in severity. Furthermore, the heat of reaction, approximately 700 kJ/mole in this process, can best be removed in this way because energy is released only in small quantities over the whole time by one specific route. It is thus possible to use specific more efficiently designed cooling.

A further, but no less important, advantage of this type of reaction regime is the possibility of operating the oxidation in continuous manner. This offers enormous advantages for large-scale industrial production of (I) in terms of space/time yield, and hence economic production.

Any apparatus known to persons skilled in the art, in which a local concentration profile which is constant as to time can be adjusted can in principle be used for this type of reaction (for example a stirred-tank reactor cascade). The use of a tubular or recycle reactor is advantageous. Such advantageous vessels are described in greater detail in FIGS. 1 and 2.

Following the latter reaction, the reaction solution which arises is extracted in direct manner with water-immiscible organic solvents. The extraction may be carried out in continuous or discontinuous manner. Since the subsequent ring-closing reaction must take place with the exclusion of water, it is particularly advantageous for the oxidation product (III) to be extracted with a solvent which is amenable to the removal of water by azeotropic distillation. Additional drying of the solvent is otherwise unavoidable. organic solvents which have proved particularly advantageous are ethyl acetate, propyl acetate, butyl acetate, methylene chloride, toluene or mixtures thereof.

The subsequent ring-closing reaction and conversion of the nitrile (III)

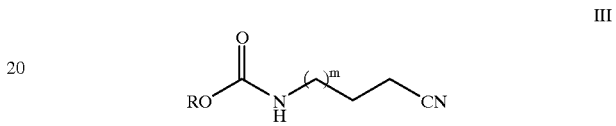

into a salt of the formula (I)

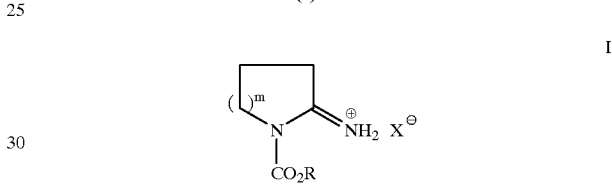

is carried out according to the invention with an inorganic acid. The use of hydrogen chloride or hydrogen bromide is most particularly preferred. According to the invention, the hydrogen chloride or hydrogen bromide is used in an excess of up to 5 times molar. The latter acids are particularly preferably used in up to 4 times excess, 3 times excess is most particularly preferred. If the substrate (III) is present in an organic solvent, it must be ensured either that the latter is removed completely after the removal of water by azeotropic distillation, and the compound (III) is reacted as such with the acid, or that after the removal of water by azeotropic distillation the organic solvent is present in the reaction only if it is stable to the latter acids. Particularly advantageous solvents are therefore solvents such as are both amenable to the removal of water by azeotropic distillation and inert to hydrogen chloride and hydrogen bromide. The use of toluene is therefore most particularly preferred for the extraction and the ring-closing reaction.

When toluene is used in combination with hydrogen chloride or hydrogen bromide, two phases form in the reaction. In the upper phase toluene is present dissolved with some hydrogen chloride or hydrogen bromide, while the lower phase contains the acid and the product (I). According to the invention, an alcohol or an ether is added to the cyclisation mixture after the cyclisation, in order to induce crystallisation. Suitable ethers in this case are in particular methyl tert.-butyl ether, 1,2-dimethoxyethane or THF, dioxane. Alcohols which are preferably used are methanol, ethanol, sec-butanol, isobutanol and, most particularly preferably, isopropanol. It is, however, also advantageous to carry out a phase separation before the crystallisation. In this case the product-containing acid phase is introduced into ethers or alcohols for crystallisation.

If the compound (III) is reacted as such with the inorganic acid, after completion of the reaction the latter mixture is added to the aforementioned ethers or alcohols, or vice versa, in order to initiate crystallisation.

It is advantageous in all the crystallisation variants to reduce the inorganic acid content of the reaction mixture under vacuum before the addition of the alcohols or ethers, in order to have the lowest possible acid content present in the crystallisation solvent. This simplifies the recycling of the latter solvents.

A vacuum is therefore preferably applied before or during the addition or the mixing of the reaction mixtures with alcohols or ethers.

Advantageous embodiments of the cyclisation reaction result if three times the stoichiometric quantity of hydrogen chloride is added to the nitrile (III) which is present in anhydrous form dissolved in toluene. The resulting two-phase mixture substantially consists of a toluene phase having a hydrogen chloride content of approx. 1.5 to 1.8% and a hydrogen chloride phase which substantially contains the product. After the reaction the majority of the hydrogen chloride is removed, by the application of a vacuum, from the two-phase mixture which resulted, with the end product beginning slowly to crystallise out. The crystallisation is speeded up and residual hydrogen chloride dissolved by the addition of THF. After separation of the solid by means of a filter, the filter cake is again washed with THF. The filter cake is then dried at 35–40°C.

An embodiment according to the invention of this process proceeds by first separating the phases of the two-phase mixture. The upper phase which substantially consists of toluene and approx. 1.5 to 1.8% HCl can be used for the next batch. Isopropanol is added in direct manner to the lower phase which substantially consists of product and hydrogen chloride, with the application of a vacuum, or the latter phase is introduced into isopropanol. Here the hydrochloride of the compound (I) precipitates out. This precipitation may take place either by dispensing the lower, organic phase into isopropanol with slight cooling at approx. 15° C., or by running the isopropanol into the organic phase. In both cases the temperature should not exceed 30° C. so as to prevent yield losses. The majority of the hydrogen chloride is removed by the vacuum which is present. Before the precipitate is separated by means of a filter or centrifuge, the suspension is first cooled to approx. 5° C. The filter cake is then post-washed with cold isopropanol and is then dried at 35 to 40° C. under vacuum. To complete crystallisation, the combined isopropanol solutions may be concentrated by evaporation at a maximum temperature of 40° C. under vacuum. Some product (I) precipitates again, and is worked to a slurry and washed with a little fresh isopropanol. The yield can be further markedly increased by the latter process. Like the toluene, the isopropanol which is distilled off can be used for the next batch without further purification.

When the compound (III) is cyclised to (I) with hydrogen chloride as such, crystallisation can take place according to the invention, as just described. The phase separation from the toluene as described is then omitted. The possibility of a continuous reaction regime is furthermore advantageous. The most particular importance of the latter working-up variant is that, with a suitably pure product, crystallisation of the salt (I) from a solvent can be omitted entirely. In this case the product-containing hydrogen chloride phase is simply supplied to spray-drying or to fluidised bed drying.

It is consequently possible, in such a simple and advantageous way for a large-scale industrial process, to produce the salt (I) in a manner which, ecologically and economically, is superior to the prior art process, as a direct result of the discovery of a suitable method for selectively protecting the ω-amino function of ω-amino-α-amino acid and the possibility of carrying out the oxidative breakdown of the derivative (II) to (III) and cyclising it to (I), followed by the improved crystallisation variant.

A linear ($C_1$–$C_4$)-alkyl radical is understood to be the methyl, ethyl, n-propyl or n-butyl radical.

Examples follow which aim to describe the invention while in no manner restricting it.

EXAMPLE 1

Batch Production of N-(4-cyanobutyl) carbamic acid methylester

An aqueous solution of 1055 g MOC-lysine in the form of a 15.42% raw solution is introduced into a flask. 319.6 g elemental bromine are dispensed-in at a maximum temperature of 35° C. within 1 h. In parallel, the pH is maintained at 9.6 by dispensing-in 533 g 30% NaOH. After dispensing is complete, stirring takes place at the same temperature for 15 to 30 minutes, and the batch is then cooled to room temperature. The aqueous phase is extracted three times, in each case with 100 ml ethyl acetate. The combined extracts are then worked up by distillation at a bottom temperature of <50° C. under vacuum. 115.6 g N-(cyanobutyl) carbamic acid methylester are obtained at 87% purity. This corresponds to an 81% yield.

EXAMPLE 2

Batch Production of N-(4-cyanobutyl) carbamic acid methylester

A solution of 2086 g bromine in 9275 g dichloromethane is introduced into a flask and cooled to approx. 10° C. Sodium hydroxide dispensing (1 l/h) commences. A total of approx. 2302 g (26.4 mole) NaOH in the form of a 50% aqueous solution are dispensed. Shortly afterwards (approx. 5 minutes), ⅓ of the quantity of MOC-lysine is dispensed in parallel, while the temperature is held at 10° C. by cooling. The second third of MOC solution can be dispensed at 15° C. and the third at 25° C. A total of 1225.38 g (6 mole) MOC-lysine in the form of an approx. 11–12% raw solution are dispensed within 2 h. After dispensing of the components, stirring takes place at 25° C. for 1 h. Precipitated salt is filtered off and is post-washed, in each case with approx. 3600 g dichloromethane. The two-phase system is then stirred intensively to extract the product. After phase separation the aqueous phase is extracted twice more with 5 l dichloromethane. The combined extracts are then concentrated by evaporation at a bottom temperature of <50° C. under vacuum. 915 g N-(cyanobutyl) carbamic acid methylester having an 87% content are obtained. This corresponds to an 85% yield.

EXAMPLE 3

A solution of 83.7 kg (96 mole) sodium chlorite as an approx. 14.25% solution and 10.3 kg (100 mole) sodium bromide dissolved in 20 l water are added to 55.7 kg (30 mole) Moc-lysine as an 11% aqueous solution at a maximum temperature of 25° C. The pH is meanwhile held at 9.7 to 10.0 with concentrated sodium hydroxide. After 10 min, 1.1 kg sodium hydrogensulphite are added to the reaction solution to remove excess oxidant, and the reaction solution is then extracted 3 times with 40 l ethyl acetate. The extract contained 3.78 kg N-(4-cyanobutyl) carbamic acid methylester (80.7%).

EXAMPLE 4

Continuous Production of N-(4-cyanobutyl) carbamic acid methylester (III) in a Tubular Reactor FIG. 1 shows a tubular reactor 1 having inlets and outlets. The inlets are controlled by way of the pumps 3, 5 and 7. The inlets of the pumps 5 and 7 may as an option be coupled by means of a static mixer and then open into the tubular reactor 1. The tubular reactor 1 consists of a jacket-type cooler 11 and is packed with a packing insert 13. An outlet 15 is attached to the tubular reactor 1. The latter outlet 15 branches to form a heat exchanger 17 and a heat exchanger 19. The heat exchanger 17 is in turn in contact with the heat exchanger 19 by way of piping and has a separate discharge 21. The heat exchanger 19 is positioned upstream of a buffer vessel 23. Downstream of the buffer vessel 23 there is located a pump 25 and an outlet 27.

1 mole, and 0.5 mole ε-Moc-lysine are dispensed per hour into the tubular reactor by way of the pump 3. As an option, bromine and sodium hydroxide may be fed by way of the pumps 5/7 into the tubular reactor either in direct manner or premixed by way of a static mixer 9 upstream of the feed. The pH in the tubular reactor is here 9.0–10. The temperature in the tubular reactor is adjusted to approx. 40° C. by means of the cooler 11. The reaction mixture is then supplied to the extraction by way of the outlet 15.

EXAMPLE 6

Production of MOC-lysine a) Two-phase Operation 3654 g (20 mole) lysine*HCl are dissolved in 9000 ml water and introduced into a 30 l stirred vessel. A pH of approx. 11.6 is adjusted with 50% sodium hydroxide, and the solution is then cooled to 14–15° C. There are then added 5406 g (60 mole) dimethyl carbonate and 3000 ml toluene at 14–15° C., and intensive stirring commences. After 7–8 h under the conditions indicated, the reaction is finished. The pH is held constant at 11.6 throughout the reaction period by dispensing a 50% sodium hydroxide solution. This required approx. 1770 g (10.77 mole) 30% sodium hydroxide.

The stirrer is switched on for working-up. After approx. 30 minutes the organic phase has separated from the aqueous phase. The lower, aqueous phase contains the product (91%), unreacted lysine (8%) and a small amount of by-products (1%), the upper, organic phase substantially consists of toluene and unreacted dimethyl carbonate (2620 g=52%). This corresponds to a DMC loss by saponification

| MOC-LYS (mole/h) | Bromine (mole/h) | Excess $Br_2$ (eq.) | T (° C.) | pH | Dwell time (min) | Selectivity (%) | MOC-LYS (%) |
|---|---|---|---|---|---|---|---|
| a) | | | | | | | |
| 1 | 4.5 | 2.25 | 40/48 | 9.1–9.3 | 8 | 80 | 17 |
| b) | | | | | | | |
| 0.5 | 2.5 | 2.5 | 35/40 | 9.0 | 6 | 82 | 7.4 |
| 0.5 | 2.5 | 2.5 | 35/40 | 9.5 | 6 | 91 | 6.7 |
| 0.5 | 2.5 | 2.5 | 35/40 | 10.0 | 6 | 90 | 6.2 |
| 0.5 | 2.5 | 2.5 | 34/33 | 9.8 | 2.8 | 79 | 24.8 | a) with static mixer 9
b) without static mixer 9

EXAMPLE 5

Figure 2:
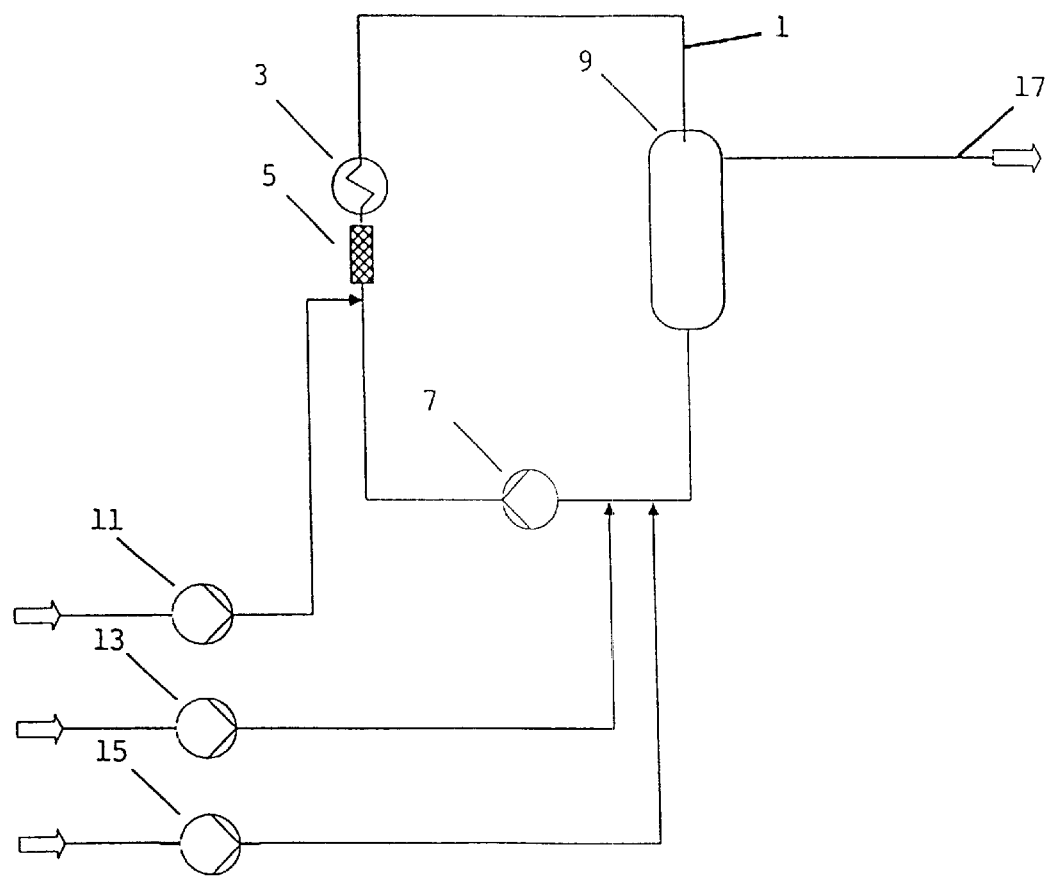

Continuous Production of N-(4-cyanobutyl) Carbamic Acid Methylester (III) in a Recycle Reactor FIG. 2 shows a recycle reactor having inputs and discharges. The recycle reactor consists of a pipe system 1 in the form of a ring. A heat exchanger 3 is integrated into the pipe system 1. A static mixer 5 is positioned downstream of the heat exchanger 3, and is followed by a pump 7 and an overflow vessel 9. The overflow vessel 9 is connected again to the heat exchanger 3 by means of a pipe system 1. There exists between the mixer 5 and the pump 7 an inlet by way of a pump 11. Two inlets from the pumps 13 and 15 exist between the pump 7 and the overflow vessel 9. The overflow vessel 9 has a discharge 17.

1.64 l ε-Moc-lysine as a 9% aqueous solution are dispensed per hour into the recycle reactor by way of the pump 11. Into this are dispensed 0.54 l 20 % NaOH by way of the pump 13 and 0.060 ml $Br_2$ by way of the pump 15. The reaction temperature is around approx. 35–40° C.

of approx. 38%. The dimethyl carbonate-containing toluene phase is made up with dimethyl carbonate and used for the next batch without further handling. The lower, aqueous phase is used for the oxidative breakdown without further handling.

b) Single-phase Operation 372 g (2.0 mole) lysine hydrochloride in 900 g water are introduced into a 2 l stirred flask. A pH of 11.6 is adjusted by the addition of 152 g (3.8 mole) sodium hydroxide. After cooling to 13–15° C., 541 g (6.0 mole) dimethyl carbonate are added, and the reaction is initiated by intensive stirring. The reaction is finished after 7 h at this temperature. The pH was held constant throughout the reaction period at 11.5–11.7 by continuous dispensing of 430 ml sodium hydroxide (10%-concentration).

The aqueous phase contains approx. 90.5% MOC-lysine, 8.5% lysine and approx. 1% by-products. The excess dimethyl carbonate had been completely saponified.

| MOC-LYS (mole/h) | Bromine (mole/h) | Excess $Br_2$ (eq.) | T (° C.) | pH | Dwell time (min) | Selectivity (%) | MOC-LYS (%) |
|---|---|---|---|---|---|---|---|
| 0.75 | 4.5 | 3 | 37–38 | 9.4–9.6 | 6.6 | 88.3 | 3.6 |

EXAMPLE 7

Cyclisation of N-(4-cyanobutyl) Carbamic Acid Methylester to N-methoxyiminopiperidine a)
31.2 g (0.2 mole) N-(4-cyanobutyl) carbamic acid methylester (85%) are dissolved in 165 ml toluene at room temperature. The solution is then cooled to 15° C., and 21.9 g (0.6 mole) hydrogen chloride are introduced for 1 h at this temperature. Stirring takes place at 15–20° C. for 1 h, with a two-phase system arising. For working-up, excess hydrogen chloride is first removed at room temperature under a vacuum of up to 100 mbar. On commencement of crystallisation, 83 ml THF are added in order to precipitate the product completely.

The precipitated product is separated and washed for a second time with 83 ml THF in order to remove the remaining hydrogen chloride residues.

The product is separated and dried at 35–40° C. under vacuum (10 mbar).

After drying, 34.7 g (90%) N-methoxyiminopiperidine salt are obtained in the form of a slightly yellowish solid.

b)
The procedure is initially analogous to Example 7a). The two phases are separated at the end of the post-reaction time. The upper, toluene phase still contains approx. 1.5–1.8% hydrogen chloride. The latter phase can be used for the next cyclisation without further handling.

The lower, product phase is dispensed into 85 ml isopropanol, with the product precipitating. In parallel with the dispensing of the product phase a vacuum of up to 100 mbar is applied in order to remove excess hydrogen chloride.

The product is separated, post-washed with 50 ml isopropanol and dried at 35–40° C. under vacuum (10 mbar).

After drying 35.6 g (92.3%) N-methoxyiminopiperidine hydrochloride are obtained in the form of a white solid.

c)
156 g (1.0 mole) N-(4-cyanobutyl) carbamic acid methylester are introduced into a flask, and 109.5 g (3.0 mole) hydrogen chloride are added at 15–20° C. within 3 h. Stirring takes place at 15–20° C. for 1 h. The reaction solution is then run into 300 ml isopropanol previously cooled to 0–5° C. A light yellow precipitate forms here. The suspension is heated to 25–30° C. Excess hydrogen chloride is removed at this temperature within 30 minutes by means of a vacuum. The suspension is cooled to 0–5° C. before the product is isolated. The isolated product is post-washed with 200 ml cold isopropanol and is dried at 35–40° C. under vacuum (10 mbar).

After drying, 175,4 g (91,1%) N-methoxycarbonyliminopiperidine hydrochloride are obtained in the form of a white solid.

d)
The procedure is as described for Example 7c. The hydrogen chloride is then, however, removed under vacuum, and the residue which remains is dried at 50° C. in a drying cupboard.

200.1 g (97.1%, 93.46%) N-(4-cyanobutyl) carbamic acid methylester are obtained.

EXAMPLE 8

Production of ε-methoxycarbonyl Ornithine 211 g (1.25 mole) ornithine hydrochloride are introduced with 400 ml water into a 2-litre stirred vessel. 400 g of 25% NaOH are dispensed-in with slight cooling. 340 g (3.75 mole) dimethyl carbonate dissolved in 300 ml toluene are then added at 15° C. The pH is held constant at 11.5 throughout the 7-hour reaction period by continuous dispensing of sodium hydroxide (25% NaOH consumed over the entire reaction period=205 ml). The phases are separated after the reaction has finished. The upper, toluene phase (378 g) still contains approx. 18% DMC (69 g). The lower, aqueous product phase still contains approx. 2.83% ornithine (39.2 g), corresponding to an 81.4% conversion.

The latter aqueous solution can be supplied without problems to the oxidative breakdown to give N-(cyanopropyl)-carbamic acid methylester. In order to isolate the MOC-ornithine, the pH is adjusted to 4.2 with hydrochloric acid, with the product precipitating. 199 g MOC-ornithine having an 87.8% content are obtained (contains 8.9% NaCl) after drying at 40° C. under vacuum. This corresponds to an isolation yield of 80.7%.

EXAMPLE 9

Production of N-(cyanopropyl)-carbamic Acid Methylester 221.2 g (1.0 mole) MOC-ornithine sodium salt are reacted in the form of a 10.56% aqueous solution in a manner analogous to Example 4. Under otherwise identical conditions, 400 g bromine (2.5 mole) and approx. 5 mole NaOH in the form of a 25% aqueous solution are dispensed additionally within the operating period.

3438 g of reaction solution are obtained. The reaction solution is extracted with acetic ester. After the extracting agent has been removed by distillation, 158 g of product (95.6%-concentration) are obtained. The yield is quantitative.

Example 10

Production of 1-methoxycarbonyl-2-iminopyrrolidine Hydrochloride 77 g hydrogen chloride are introduced, with slight cooling, into 155 g (1.04 mole) N-(cyanopropyl)-carbamic acid methylester in 200 ml toluene at 20° C. During this procedure the product precipitates after only a short time. It is worked up as normal. 180 g of product are obtained. This corresponds to a yield of 93%.

What is claimed is:

1. A process for the production of a salt of formula (I)

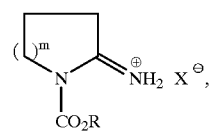

wherein $X^{\ominus}$ represents an inorganic anion, m=1, 2, or 3, and R represents a linear $(C_1–C_4)$-alkyl radical, which comprises:

a) reacting an ω-amino-α-amino acid with a compound of formula (IV)

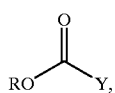

wherein Y=Cl, Br or OMe or

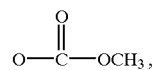

and R is linear $(C_1–C_4)$-alkyl radical or an aryl radical to give a compound of formula (II)

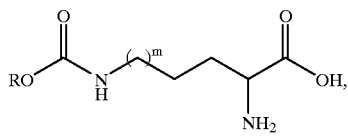

b) oxidizing the compound of formula (II) to give a compound of formula (III)

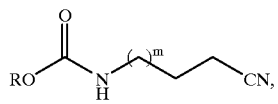

c) cyclizing the compound of formula (III) in the absence of water in the presence of an acid by ring closure to give the salt compound of formula (I).

2. The process according to claim 1, wherein the ω-amino-α-amino acid is lysine.

3. The process according to claim 1, wherein the reaction of said ω-amino-α-amino acid is conducted in a two-phase system prepared from water and a water-immiscible organic solvent.

4. The process according to claim 1, wherein the reaction of said ω-amino-α-amino acid is conducted in a single-phase system prepared from water and optionally a water-miscible organic solvent.

5. The process according to claim 1, wherein the compound of formula (IV) is present in the reaction in an amount of an excess of 1–10 equivalents based on the amount of ω-amino-α-amino acid employed.

6. The process according to claim 5, wherein said amount of compound of formula (IV) is 3–5 equivalents in excess of the amount of ω-amino-α-amino acid.

7. The process according to claim 2, wherein the reaction of step (a) occurs at a pH greater than 8 but less than 14.

8. The process according to claim 7, wherein said reaction occurs at a pH ranging from 10 to 13.

9. The process according to claim 11, wherein the temperature for the reaction of step (a) ranges from 5 to 25° C.

10. The process according to claim 9, wherein said temperature range is from 10 to 20° C.

11. The process according to claim 1, wherein the compound of formula (II) is oxidized with a halogen or halogen compound oxidant thereby yielding the compound of formula (III).

12. The process according to claim 11, wherein the compound of formula (II) is oxidized in an aqueous solution optionally containing an organic solvent.

13. The process according to claim 12, wherein the compound of formula (II) is isolated as a solid before oxidation.

14. The process according to claim 12, wherein the compound of formula (II) is oxidized without intermediate isolation.

15. The process according to claim 11, wherein the temperature for reaction of step (b) ranges from –10 to 60° C.

16. The process according to claim 15, wherein said temperature ranges from 20 to 50° C.

17. The process according to claim 11, wherein the amount of said oxidant is in excess of 2–4 equivalents based on the amount of compound of formula (II).

18. The process according to claim 17, wherein the amount of said oxidant is 2–3 equivalents in excess of the amount of said compound of formula (II).

19. The process according to claim 18, wherein the amount of said oxidant is 2–2.5 equivalents in excess of the compound of formula (II).

20. The process according to claim 11, wherein the pH of the oxidation medium of step (b) ranges from 6 to 13.

21. The process according to claim 20, wherein said pH ranges from 7 to 11.

22. The process according to claim 21, wherein said pH ranges from 8 to 10.

23. The process according to claim 11, wherein the reaction of the oxidation step is conducted in a batch-wise fashion.

24. The process according to claim 11, wherein the oxidation reaction is conducted such that the reaction components have a local concentration profile in which the concentrations of reactants in a given location are constant over time.

25. The process according to claim 24, wherein the oxidation reaction is conducted in a recycle or tubular reactor.

26. The process according to claim 1, wherein the compound of formula (III) is converted into the salt of formula (I) by means of an inorganic acid.

27. The process according to claim 26, wherein said inorganic acid is hydrogen chloride or hydrogen bromide.

28. The process according to claim 27, wherein said acid is present in an amount in excess of up to 5 equivalents based on the compound of formula (III).

29. The process according to claim 28, wherein said amount of acid is in excess of 2–3 equivalents based on the amount of compound of formula (III).

30. The process according to claim 26, wherein said acid is added to the compound of formula (III) dissolved in a water-immiscible organic solvent.

31. The process according to claim 30, wherein said acid is added to the compound of formula (III).

32. The process according to claim 30, wherein the reaction of step (c) is conducted at a temperature ranging from 10 to 30° C.

33. The process according to claim 32, wherein said reaction is conducted at a temperature of 15 to 20° C.

34. The process according to claim 30, wherein the salt of formula (I) is crystallized by the addition of an ether and/or alcohol to the reaction mixture.

35. The process according to claim 34, wherein a vacuum is applied to the reaction of step (c) before or during the addition of alcohol and/or ether thereto.

36. The process according to claim 31, wherein the product-containing hydrogen chloride is spray dried or dried in a fluidized bed.

* * * * *